United States Patent [19]

Tanaka et al.

[11] Patent Number: 5,037,754
[45] Date of Patent: Aug. 6, 1991

[54] CULTURE VESSEL

[75] Inventors: Michio Tanaka, Kida; Tadashi Higashiura, Ibaraki, both of Japan

[73] Assignee: Daikin Industries Ltd., Japan

[21] Appl. No.: 546,695

[22] Filed: Jul. 2, 1990

Related U.S. Application Data

[63] Continuation of Ser. No. 187,255, Apr. 28, 1988, abandoned, which is a continuation of Ser. No. 919,870, Oct. 17, 1986, abandoned.

[30] Foreign Application Priority Data

Oct. 19, 1985 [JP] Japan .................. 60-160518
Oct. 19, 1985 [JP] Japan .................. 60-160519

[51] Int. Cl.⁵ .................................................. C12N 5/00
[52] U.S. Cl. ................................. 435/240.4; 435/296; 47/58
[58] Field of Search ............... 435/285, 291, 296, 297, 435/298, 299, 300, 301, 313, 240.4, 240.45, 240.5; 215/1 C; 206/423, 439; 220/DIG. 11, DIG. 14; 521/145; 526/246, 247, 254; 47/58

[56] References Cited

U.S. PATENT DOCUMENTS

| | | | |
|---|---|---|---|
| 2,781,552 | 2/1957 | Gray | 18/55 |
| 2,851,821 | 9/1958 | Guiochon | 47/1.1 |
| 3,184,395 | 5/1965 | Brewer | 435/299 |
| 3,235,636 | 2/1966 | Trimble | 264/87 |
| 3,338,794 | 8/1967 | Bladel | 435/299 |
| 3,433,712 | 3/1969 | Gerarde | 435/292 |
| 3,684,660 | 8/1972 | Kereluk et al. | 435/298 |
| 3,855,191 | 12/1974 | Doughty, Jr. et al. | 260/87.5 A |
| 3,870,602 | 3/1975 | Froman et al. | 435/299 |
| 3,941,662 | 3/1976 | Munder et al. | 435/808 |
| 3,951,293 | 4/1976 | Schulz | 215/261 |
| 4,140,489 | 2/1979 | Lee | 435/39 |
| 4,435,508 | 3/1984 | Gabridge | 435/285 |
| 4,552,925 | 11/1985 | Nakagawa et al. | 526/247 |
| 4,612,357 | 9/1986 | Bekiarian et al. | 526/247 |
| 4,748,124 | 5/1988 | Vogler | 435/285 |

FOREIGN PATENT DOCUMENTS 2541000 11/1976 Fed. Rep. of Germany.
1312447 4/1973 United Kingdom.

OTHER PUBLICATIONS

Neoflon TM PFA, Technical Information EG-64b Daikin Ind., Ltd. 7/87.
Neoflon TM FEP Film, Technical Information EG-62C Daikin Ind., Ltd. 4/86.
Neoflon TM FEP Pellets, Technical Information EG-61f Daikin Ind., Ltd. 4/88.

Primary Examiner—Noah P. Kamen
Attorney, Agent, or Firm—Birch, Stewart, Kolasch & Birch

[57] ABSTRACT

A culture vessel at least a part of which comprises a film a fluorine-containing melt processable resin, which is suitable for culturing which requires gas permeability.

1 Claim, 2 Drawing Sheets

CULTURE VESSEL

This application is a continuation of application Ser. No. 07/187,255 filed on Apr. 28, 1988, now abandoned, which is a continuation of application Ser. No. 06/919,870 filed on Oct. 17, 1986, abandoned.

BACKGROUND OF THE INVENTION

1. Field of the Invention

The present invention relates to a culture vessel. More particularly, present invention relates to a gas permeable culture vessel at least a part of which comprises a film of a fluorine-containing melt processable resin.

2. Description of the Prior Art

Since a culture vessel provides an environment in which animal or plant cells, tissues or organs, or microorganisms are cultured, it is necessary that it have various properties such as high light transmission, low water vapor transmission, durability and chemical resistance. A glass or plastic vessel has these properties and has been and is widely used. Since the culture vessel has an opening through which a culture medium and the like are poured, the opening is usually air exchangeably closed with a cotton plug, a rubber plug having a bore filled with cotton or a paper plug, or covered with a sheet of aluminum foil. For air exchangeable closing of the opening of the vessel, proposed is a rubber plug a center of which is bored and sealed with a sheet of open cell foam.

However, in conventional closing manners, the culture in the vessel is often contaminated with microorganisms by air flow caused by temperature change. In addition, the glass vessel tends to be easily broken, and its shape is limited to a bottle or a tube because of its poor processablity.

SUMMARY OF THE INVENTION

Accordingly, one object of the present invention is to provide a culture vessel having light transmission as good as glass, gas permeability without contamination, and low water vapor transmission.

Another object of the present invention is to provide an unbreakable culture vessel.

A further object of the present invention is to provide a culture vessel a shape of which can be freely designed.

These and other objects are accomplished by providing a culture vessel at least a part of which comprises a film of a fluorine-containing melt processable resin. In the present invention, the culture vessel includes not only the vessel itself but also any element which composes the culture vessel such as a vessel body and a cap or a plug.

DETAILED DESCRIPTION OF THE INVENTION

According to the present invention, at least a part of the culture vessel comprises a film of a fluorine-containing melt processable resin.

Specific examples of the fluorine-containing melt processable resin are copolymers of tetrafluoroethylene and hexafluoropropylene (hereinafter referred to as "FEP"); copolymers of tetrafluoroethylene and perfluoro(alkyl vinyl ether) (hereinafter referred to as "PFA"), particularly copolymers of tetrafluoroethylene and perfluoro(propyl vinyl ether); copolymers of ethylene, tetrafluoroethylene and at least one of other fluoroolefines; and fluorine-containing acrylic resins, for example, polymers comprising repeating units of the formula:

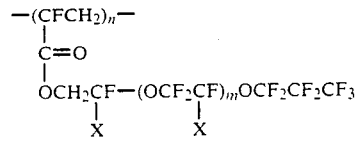

wherein m is an integer of 0 to 5, and X is a fluorine atom or a trifluoromethyl group.

The fluorine-containing melt processable resin has low water vapor transmission and gas permeability sufficient for cultures so that they are suitable for cultures which require gas permeability.

The culture vessel of the present invention may consist of only one part or two or more parts such as a combination of a body of the vessel and a sealing member or of a body of the vessel and a metal or resin frame for supporting the vessel body. In this context, the sealing member is intended to mean any element that seals or covers an opening of the vessel body and includes a cap for closing the opening and a sheet or a film made of the fluorine-containing melt processable resin which covers the opening.

The culture vessel of the present invention may consist of a continuous film of the fluorine-containing melt processable resin alone or a integrated film at least one of which is made of the fluorine-containing melt processable resin and the rest of which is made of other resin. When the culture vessel has the sealing member, only at least a part of the sealing member comprises a film of the fluorine-containing melt processable resin and the vessel body may be made of a suitable material, particularly a resin.

Generally, the film of the fluorine-containing melt processable resin has a thickness of 2 to 2,500 micrometers, preferably 4 to 100 micrometers.

The films of the fluorine-containing melt processable resin can be easily processed by welding, heat bonding, adhesion with an adhesive, molding and the like. Therefore, the culture vessel of the present invention can have various shapes.

The culture vessel of the present invention may be used in the same field as the conventional glass culture vessel.

A preferred embodiment of the culture vessel of the present invention will now be described, by way of example, with reference to the accompanying drawings.

FIGS. 1 to 5 show perspective views of several culture vessels of the present invention. A film composing each culture vessel 1, 2, 3, 4 or 5 may be made of the fluorine-containing melt processable resin alone or a laminate film containing at least one layer of the fluorine-containing melt processable resin.

Figure 1:
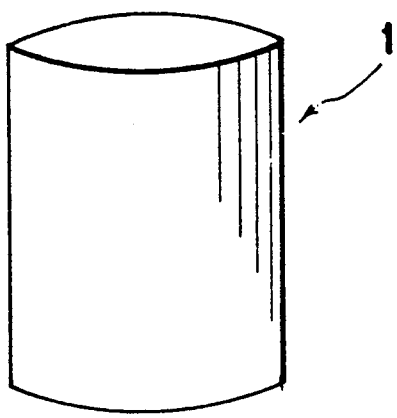
FIG. 1 is a perspective view of an envelope type culture vessel according to the present invention.
Figure 2:
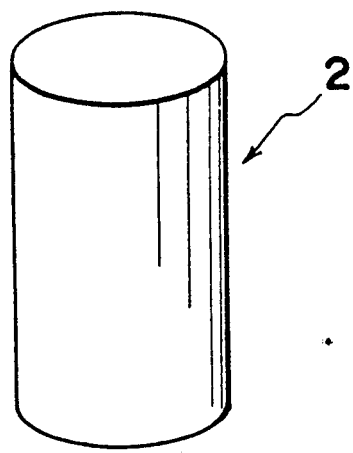
FIG. 2 is a perspective view of a cylindrical culture vessel according to the present invention.
Figure 3:
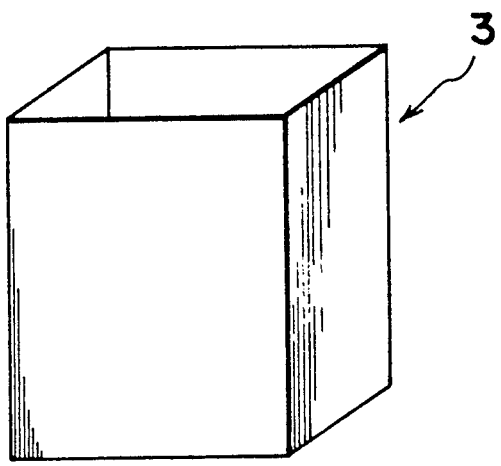
FIG. 3 is a perspective view of a square pillar type culture vessel according to the present invention.
Figure 4:
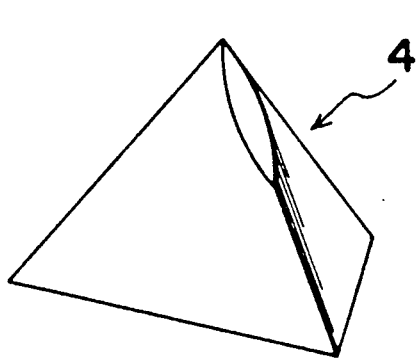
FIG. 4 is a perspective view of a tetrahedral culture vessel according to the present invention.
Figure 5:
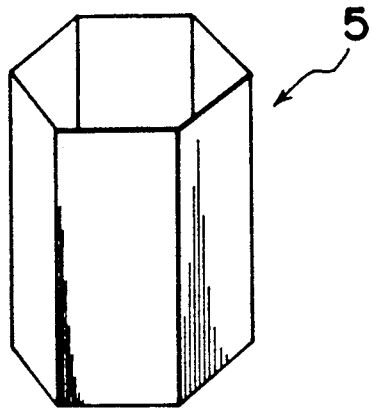
FIG. 5 is a perspective view of a hexagonal pillar type culture vessel according to the present invention.

The envelope type culture vessel of FIG. 1 is particularly advantageous because it can be stacked with another one and occupies only a small space in a chamber, and is convenient to culture many portions of the culture medium each having a small volume. The square pillar type culture vessel of FIG. 3 or the hexagonal pillar culture vessel of FIG. 5 is set side by side without any gaps between the adjacent vessels so that they effectively occupy a culture space such as a shelf in an environmentally controlled chamber.

After a culture medium is poured and then explants and the like to be cultured are inoculated in the culture vessel, the opening of the vessel is closed by any method insofar as air-inflow or contamination of the vessel by the microorganisms is substantially prevented, for example by heat bonding the film near the opening or by the use of the sealing member. When using the sealing member, a neck opening is provided with on a wall of the vessel as in the case of the plastic culture vessel, and the medium is poured through the neck opening and then the explant and the like to be cultured are inoculated. Thereafter, the neck opening is closed with a cap. The neck opening and the cap are preferably made of a resin.

Alternatively, an opening is made on a wall of the culture vessel. In this case, after the medium and the like are charged, the opening can be sealed with a sheet or a film of a suitable material having a slightly larger area than that of the opening. The sheet or film for sealing the opening may be preattached over the opening by adhering or welding a part of the sheet or film to a part of the wall around the opening.

Figure 6:
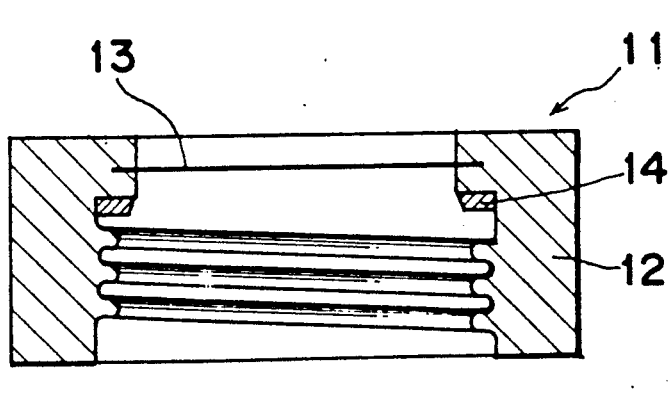
FIG. 6 shows a cross section of a plug a top wall of which is made of a film of a fluorine-containing melt processable resin.

FIG. 6 shows a cross section of a cap 11, a top wall 13 which consists of a film of the fluorine-containing melt processable resin and attached to a body of the cap 12. The cap 12 also contains a packing 14 made of a resilient material.

The present invention will be hereinafter explained further in detail by following examples.

REFERENCE EXAMPLE 1

Light Transmission

Figure 7:
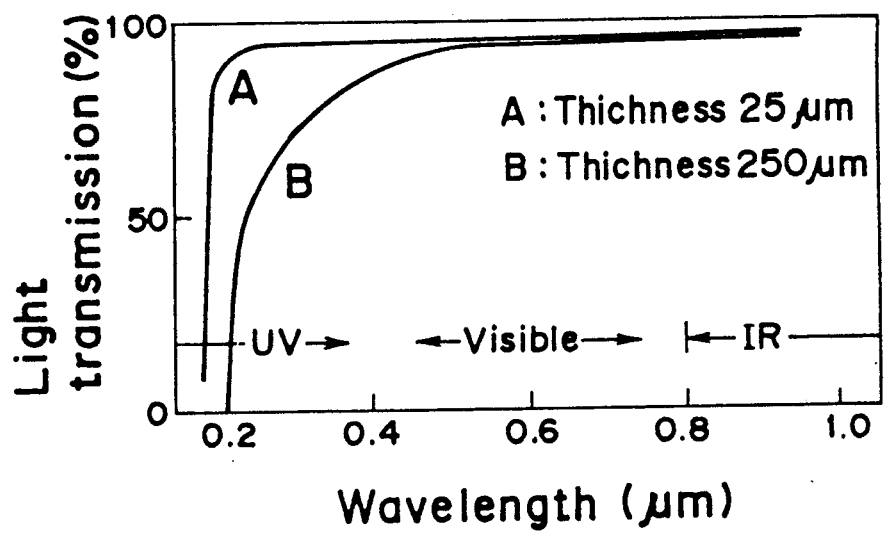
FIG. 7 is a graph showing light transmission of films of a copolymer of tetrafluoroethylene and hexafluoropropylene.
Figure 8:
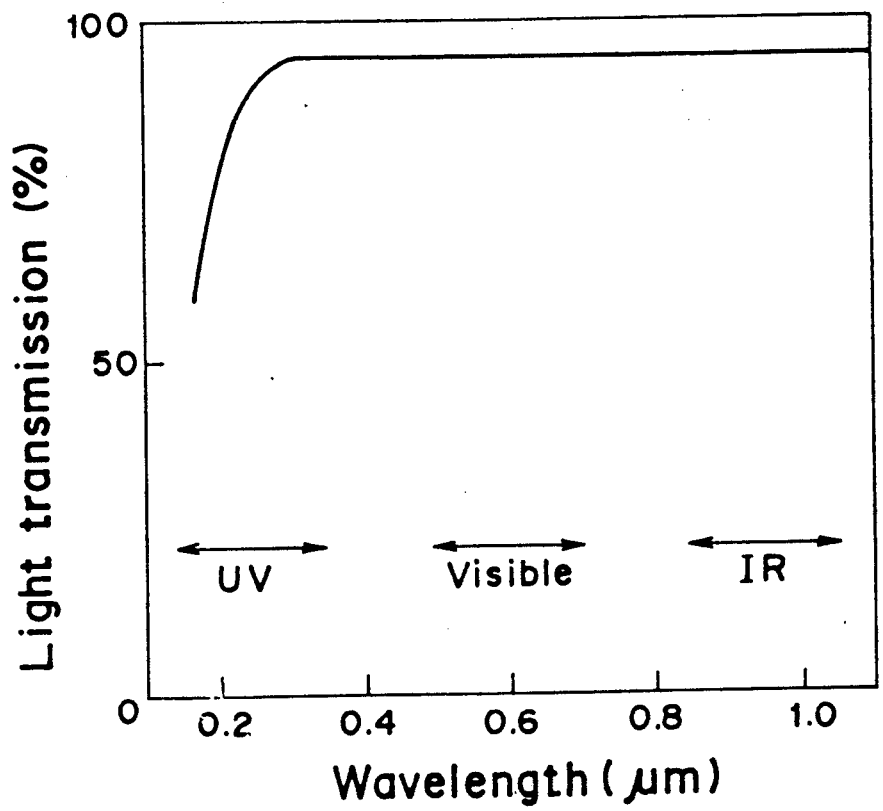
FIG. 8 is a graph showing light transmission of a film of a copolymer of tetrafluoroethylene and perfluoro(propyl vinyl ether).

Two films of FEP each having a thickness of 25 micrometers or 250 micrometers and a film of PFA (a copolymer of tetrafluoroethylene and prefluoro(propyl vinyl ether)) having a thickness of 25 micrometers were tested on their light transmission in a wavelength range shorter than 1.0 micrometer. The results are shown in FIGS. 7 and 8, respectively.

From these results, it is found that the fluorine-containing melt processable resin has good light transmission in a wavelength band from infrared to ultraviolet.

REFERENCE EXAMPLE 2

Gas Permeability

According to ASTM D 1434, the gas permeability coefficient ($cm^3 \cdot cm/cm^2 \cdot sec \cdot atm$) of FEP and PFA (the same as in Example 1) was measured for nitrogen, oxygen or carbon dioxide. The results are as follows:

| FEP | |
|---|---|
| Nitrogen: | $120 \times 10^{-10}$ |
| Oxygen: | $370 \times 10^{-10}$ |
| Carbon dioxide: | $970 \times 10^{-10}$ |
| PFA | |
| Nitrogen: | $140 \times 10^{-10}$ |
| Oxygen: | $480 \times 10^{-10}$ |

From these results, it is found that the fluorine-containing melt processable resin has good gas permeability.

REFERENCE EXAMPLE 3

Water Vapor Transmission

According to JIS Z 0208, water vapor transmission of a film of FEP and a film of PFA (the same as in Example 1) each having a thickness of 45 micrometers was measured. The results are as follows:
FEP: 2.0 $g/m^2 \cdot 24$ hours
PFA: 3.1 $g/m^2 \cdot 24$ hours
From these results, it is found that the fluorine-containing melt processable resin has good water vapor transmission.

EXAMPLE 1

A film of Neoflon (trade mark) FEP (manufactured by Daikin Industries, Ltd.) having a thickness of 100 micrometers was heat bonded by an impulse sealer to form two envelope type culture vessels, one corner of the upper edge of which was cut slantingly. The width of the film heat sealed was 5 mm. The length of the longer vertical edge (uncut side) of each envelope was 15 cm, that of the shorter vertical edge (cut side) was 8 cm, that of the cut opening was 4 cm, and that of the lower horizontal edge was 8 cm. The vessels were sterilized in an autoclave at 121° C. for 15 minutes. Then, each 80 ml of the modified Vacin and Went liquid culture medium having the below described composition was poured into the vessels. Then, 60 pieces of explants were planted in each vessel. After purging air in the upper space in the vessel, the opening was sealed with a closing element (made by Spectrum Medical Industries) and heat bonded. The explants used in this example were segments of protocorm like body (PLB) of Cymbidium Showgirl "Husky Honey". Each of PLBs (average diameter, 2.4 mm; average weight, 7.3 mg) was longitudinally divided into four after one month subculture and used as explants.

The pieces of the explants were cultured at 25° C. for 75 days under 900 lux (illuminating for 16 hours a day). The total number of the survived explants in the two vessel was 113, and the average number of PLBs proliferated from one explant was 11.9.

| Composition of the modified Vacin and Went medium | |
|---|---|
| $Ca_3(PO_4)_2$ | 200 mg/l |
| $KNO_3$ | 525 mg/l |
| $KH_2PO_4$ | 250 mg/l |

| Composition of the modified Vacin and Went medium | |
|---|---|
| MgSO$_4$.7H$_2$O | 250 mg/l |
| (NH$_4$)$_2$SO$_4$ | 500 mg/l |
| FeSO$_4$.7H$_2$O | 28 mg/l |
| MnSO$_4$.4H$_2$O | 7.5 mg/l |
| Nitsch micro elements (1967) | |
| stock solution*[1] | 1 ml/l |
| Tripton*[2] | 2 g/l |
| sucrose | 20 g/l |
| α-naphthaleneacetic acid | 0.1 mg/l |
| kinetin | 0.1 mg/l |
| (pH 5.3) | |

*[1] Composition of Nitsch micro elements (1967)
H$_2$SO$_4$  0.5 ml
MnSO$_4$.4H$_2$O  3000 mg
ZnSO$_4$.7H$_2$O  500 mg
H$_3$BO$_3$  500 mg
CuSO$_4$.5H$_2$O  25 mg
Na$_2$MoO$_4$.2H$_2$O  25 mg
Distilled water  1000 ml
*2) Manufactured by Difco Laboratories.

EXAMPLE 2

In the same manner as in Example 1 but using a film of Neoflon (trade mark) PFA (a copolymer of tetrafluoroethylene and prefluoro(propyl vinyl ether) manufactured by Daikin Industries, Ltd.) in place of the film of Neoflon FEP, making and using three culture vessel and culturing the explants for 65 days, the explants were cultured. The total number of the survived explants in the three vessels was 163, and the average number of PLBs proliferated from one explant was 15.7.

COMPARATIVE EXAMPLE

In the same manner as in Example 1 but using, as a culture vessel, two 300 ml Erlenmeyer flasks a mouth of which was covered with a sheet of aluminum foil, the explants were cultured. The total number of the survived explants was 102, and the average number of PLB proliferated from one explant was 9.0.

EXAMPLE 3

A square pillar culture vessel was formed from a film of Neoflon (trade mark) FEP.

The film was folded into a square pillar form without a top and a bottom and the overlapped edges were heat sealed with a width of about 5 mm. Two opposite edges of the bottom part were inwardly folded, and overlapped and heat sealed together with the remaining edges with a width of about 5 mm from the edge front to close the bottom. The inner sizes of the vessel were as follows:

Bottom: 7.5 cm×7.5 cm
Height: 20 cm

To prevent collapsing of the vessel, a frame of outer sizes of 7.5 cm×7.5 cm×10.5 cm made of stainless steel wire of 2 mm in diameter was placed in the vessel.

After pouring 100 ml of an agar medium having the below described composition into the vessel, the vessel was sterilized in an autoclave at 121° C. for 15 minutes.

Thereafter, in the vessel, nine plantlets of Cymbidium Valley Flower "Cherry Ripe" having 2 or 3 true leaves each having a length of about 2 cm were planted on the medium with substantially equal intervals, and the top opening was closed by the impulse sealer. Then, the plantlets were grown at 25° C. for 4 months under 2,000 lux (illuminating 16 hours a day). The observation of the size and appearance of the plants confirmed that they were normally grown without any malformation.

| Composition of the Culture Medium | |
|---|---|
| Hyponex*[1] | 3 g/l |
| (N:P$_2$O$_5$:K$_2$O = 7:6:19) | |
| Tripton*[2] | 2 g/l |
| banana | 100 g/l |
| sucrose | 20 g/l |
| agar-agar | 10 g/l |
| (pH 5.0) | |

*[1] Manufactured by The Hyponex Company Inc.
*[2] Manufactured by Difco Laboratories.

EXAMPLE 4

In the same manner as in Example 3 but using, as a culture vessel, a glass beaker having a diameter of 8 cm and a depth of 13 cm covered with a film of Neoflon (trade mark) PFA having a thickness of about 4 micrometers with completely sealing a gap between the beaker and the film with an adhesive tape, the plantlets were cultured for 4 months. The observation of the size and appearance of the plants confirmed that they were normally grown without any malformation.

EXAMPLE 5

Into a 500 ml Erlenmeyer flask having a mouth of 29 mm in diameter, there was poured 100 ml of a culture medium (pH 6.0) containing 2% of peptone, 2% of yeast extract and 4% of glucose. After the mouth of the flask was covered with a sheet of aluminum foil and the vessel was sterilized in an autoclave at 121° C. for 15 minutes, a loopful of *Saccharomyces cerevisiae* IFO 0309 strain was inoculated. Then, the sheet of the aluminum foil was replaced with a film of Neoflon (trade mark) PFA having a thickness of 4 micrometers and the gap between the flask and the film was completely sealed with an adhesive tape. The strain was cultured with shaking at 200 rpm at 35° C. for 48 hours. The strains were propagated normally, and any contamination with foreign microorganisms was not observed.

EXAMPLE 6

In the same manner as in Example 5 but using *Rhodotorula mucilaginosa* AHU 3946 strain in place of the *Saccharomyces cerevisiae* strain, the culture was carried out. The strain was propagated normally, and contamination with foreign microorganisms was not observed.

What is claimed is:

1. A method for culturing explants which comprises illuminating explants in a culture vessel; at least a part of said culture vessel comprising a gas permeable light transmitting film of a fluorine-containing melt processable resin having a thickness of 2 to 2500 micrometers.

* * * * *